United States Patent [19]
Hacker et al.

[11] Patent Number: 5,622,704
[45] Date of Patent: Apr. 22, 1997

[54] ANXIOLYTIC

[75] Inventors: Rudiger Hacker, Herrsching; Claudia Mattern, Starnberg, both of Germany

[73] Assignee: Arrowdean Limited, Dublin, Ireland

[21] Appl. No.: 367,241

[22] PCT Filed: May 24, 1994

[86] PCT No.: PCT/EP94/01690

§ 371 Date: Feb. 24, 1995

§ 102(e) Date: Feb. 24, 1995

[87] PCT Pub. No.: WO94/27625

PCT Pub. Date: Dec. 8, 1994

[30] Foreign Application Priority Data

May 28, 1993 [DE] Germany .......................... 43 17 868.5

[51] Int. Cl.$^6$ .................................................. A61K 35/78
[52] U.S. Cl. ...................... 424/195.1; 514/906; 514/923
[58] Field of Search ...................... 424/195.1; 514/906, 514/923

[56] References Cited

U.S. PATENT DOCUMENTS 4,639,466  1/1987  Huarge et al. ...................... 514/456

FOREIGN PATENT DOCUMENTS 3626128  2/1988  Germany .

OTHER PUBLICATIONS

Notice of Opposition.
Santa V, Dr. Carlos E. Pietra et al., *Eficacia del extracto estandarizado de Ginkgo–Biloba EGB 761\* en el tratamiento de la insuficiencia vascular cerebral*, Investigation Medica International, vol. 17, No. 3, (1990), pp. 130–141.
Warburton, D.M., *Psycnh–pharmacologie clinique de i'extrait de Ginkgo biloba*, La Presse Medicale, Bd. 15, Nr. 31, (1986), pp. 1595–1604.
Eckmann, Von F., *Hirnleistungsstörungen–Behandlong mit Ginkgo–biloba–Extrakt*, Fortschritte der Medizin, Bd. 108, Nr. 29, (1990), pp. 557–560.
Schenker, H., *Akt. Gerontol*, 13, (1983), pp. 104–107.
Vorberg, G. et al., *Wirksamkeit eines neunen Ginkgo–biloba–Extraktes bei 100 Patienten mit zerebraler Insuffzienz*, Herz + Gerässe, Sonderdruck aus Heft, (Jul. 1989), pp. 3–9.
Eckmann, Von. F. et al., *Kontrollierte Doppelblind–Studie zum Wirksamkeitsnachweis von Tebonin forte bei Patienten mit zerebrovaskulärer Insuffizienz*, Fortschritte der Medizin, Bd. 100, Nr. 133, (1991), pp. 1474–1478.
Schmidt, U et al., *Einfluss eines Ginkgo–Spezialextraktes auf die Befindlichkeit bei zerebraler Insuffizienz*, Munchener Medizinische Wochenschrift, Nr. 133, (1991), pp. 15–18.
*Hagers Handbuch der Pharmazeutischen Praxis*, Bd. 6, (1979), p. 574.
Yamahara, Johji et al., *Cholagogic Effect of Ginger and Its Active Constituents*, Journal of Ethnopharmacology, Nr. 13, (1985), pp. 217–225.
Grontved, Aksel et al., *Ginger Root Against Seasickness*, Acta Otolaryngol (Stockh), Nr. 105, (1988), pp. 45–49.
R. Saller et al., "*Anwendung von Ingwerpräparaten*", Intemistische Praxis, Nr. 32, (1992), pp. 386–387.
Fischer–Rasmussen, Wiggo et al., *Ginger treatment of hypermesis gravidarum*, European Journal of Obstetrics & Gynecology and Reproductive Biology, Nr. 38, (1990), pp. 19–24.
Mowrey, Daniel B. et al., *Motion Sickness, Ginger, and Psychophysics*, The Lancet, März 1982, pp. 655–657.
Yamahara, Johji et al., *Gastrointestinal Motility Enhancing Effect of Ginger and Its Active Constitutents*, Chem. Phar. Bulletin, Nr. 38(2), (1990), pp. 430–431.
Chem Abst. 119(11):109013h, 1993.

*Primary Examiner*—John W. Rollins
*Attorney, Agent, or Firm*—Merchant, Gould Smith, Edell, Welter & Schmidt, P.A.

[57] ABSTRACT

Use of a medicament with a content of active substances from Rhizoma zingiberis and Ginkgo bilobae for the treatment of anxiety states.

13 Claims, 1 Drawing Sheet

ANXIOLYTIC

The invention relates to a novel use of a combination product with active substances constituted by Rhizoma zingiberis and Ginkgo bilobae for the treatment of anxiety states.

Fear and anxiety states are typical human phenomena which, as a result of their secondary phenomena in the form of behavioural changes and disturbances in the vegetative nervous system, lead to a marked decrease in the quality of life. Triggered by overwork, compulsive situations, failures in professional and private life and other stress effects typical psychosomatic symptoms are manifested. These include escape and avoidance reactions, as well as disturbances in the vegetative field, such as intestinal and stomach complaints or the proverbial "lump in the throat".

When the triggering or provoking factors are accumulated there can be a psychovegetative exhaustion-syndrome, which is characterized by a decrease in efficiency with psychic and vegetative disturbances such as headaches, stomach pains, lack of concentration, irritability and sleep disturbances.

The biochemical, pharmacological and neurophysiological mechanisms forming the basis for this syndrome have not been completely clarified and are probably also not of a unitary nature. It can fundamentally be assumed that the homoeostatis of the neurotransmitter systems noradrenaline, dopamine and 5-hydroxytryptamine is disturbed. It is also assumed that apart from the action via the monoaminergic synopses the endogenic γ-aminobutyric acid and/or transmitter systems interacting therewith participate in provoking the symptoms. Information exists showing that in such situations the blood-brain barrier becomes more permeable for low molecular weight peptides, so that the latter can have effects on the central nervous plane.

For the therapy of psychoreactive disturbances at present only medicaments are used which belong to the group of psychopharmaceuticals. The preferred group consists of tranquillizers, also known as anxiolytics, with the benzodiazepines and their derivatives most frequently used in this field throughout the world. These active substances act in the metabolism of the endogenic γ-aminobutyric acid in that they react with specific bonding points belonging to a complex comprising the GABA receptor, benzodiazepine receptor and an ion channel for chloride ions. These receptors are present throughout the central nervous system.

Depending on the extent to which these symptoms apply use is also made of neuroleptics, which act in regularizing manner in the monoamine metabolism, such as phenothiazines. If there is a deficiency of catecholamines and serotonin (5-hydroxytryptamine) therapeutic results can be achieved with derivatives of phenothiazine, i.e. tricyclic antidepressants.

In the field of phytopharmaceuticals antidepressive actions are only attributed to St. John's wort. In the foreground there is an improvement on the mood, but opinions concerning neurovegetative actions are not uniform and in part in dispute.

It is generally considered disadvantageous in the hitherto used medicamentus treatment that the tranquillizers, as well as neuroleptics and antidepressants, apart from their desired main action, i.e. anxiolysis, lead to a number of undesired side effects. These in particular include sedation, which leads to tiredness and an increased need for sleep. The muscle-relaxing action can have an unfavourable effect in high dosages. As a result of the usually long-lasting therapy, the hepatic metabolism is significantly stressed.

In addition, tranquillizers closely interact with other centrally acting pharmaceuticals, such as hypnotics, as well as analgesics, stimulants and alcohol. Generally the effects of these substances are reinforced and in part there are even effects, which are not or only slightly noticed after administering the individual substances.

This situation has led to a worldwide search for further substances and/or derivatives of known active substances in order to minimize these disadvantages. The problem of the present invention is to meet this need.

According to the invention this problem is solved by the use of a medicament with a content of active substances from Rhizoma zingiberis and Ginkgo bilobae. Preferably the medicament contains a combination of extracts of Rhizoma zingiberis and Ginkgo bilobae.

The invention proposes that the active substances and/or extracts be available in an ingestion unit in capsule form or other solid or liquid medicinal forms suitable for peroral administration.

In the use according to the invention the preferred Rhizoma zingiberis extract content is between 50 and 200 mg and even more preferred 100 mg per ingestion unit. The Ginkgo bilobae extract content is preferably between 10 and 100 mg, more preferably 40 mg per ingestion unit. According to a preferred embodiment of the invention the Rhizoma zingiberis extract is obtained from an ethanol/water or acetone/water extraction and is essentially present as oleoresin.

Alternatively, according to the invention the Rhizoma zingiberis extract is obtained by extraction with $CO_2$.

The oleoresin or $CO_2$ extract of Rhizoma zingiberis can be transformed into a suitable galenic form by microencapsulation, granulation or lyophilization.

The combination product according to the invention is already known per se from DE 36 26 128 C2 as a medicament against nausea and vomiting. Completely surprisingly recent clinical research has established that this active substance combination in the case of a suitable composition also has an anxiolyric action, which is largely free from the described side effects, particularly of benzodiazepines.

This action is surprising for the expert, because it cannot be derived from the hitherto known actions of the two individual extracts and from the combination product and the basic biochemical mechanisms.

The ginger rhizome and the medicaments prepared from ginger (powders, tinctures, extracts, infusions) have a strong antiemetic action, suppress the cough reflex and are known as stomachic, tonic and digestive agents in the case of loss of appetite, subacid gastritis and dyspepsia.

In addition to ginger are also attributed a cardiotonic (positive inotropic) action, as well as the favouring of the circulation, together with positive effects on the absorbtion and distribution of other medicaments. The digestive process is encouraged by ginger, also through the acceleration of the biliary flow and the natural content of proteases. An inhibition of prostaglandin biosynthesis is also initiated.

From the literature the following action spectrum is known:

An ethanolic extract of Rhizoma zingiberis has the following pharmacodynamic characteristics:

antiserotoninergic actions with particular affinity for 5-HT-3-receptors on the peripheral plane, inhibiting the release of prostaglandins from leucocytes, inhibiting thrombocyte aggregation, regularizing prostaglandin synthesis, influencing vasomotor centres, normalizing central nervous blood flow.

An anxiolytic effect cannot be expected on the basis of this action spectrum.

The Ginkgo extract has a differentiated pharmacological action profile, including metabolic and hormonal regulation mechanisms, which influence the characteristics of membranes, vessel walls, blood and tissue fluids.

The following indications apply:

peripheral and arterial circulatory disturbances with blood flow reserves still maintained, brain capacity disturbances with decreasing intellectual efficiency, particularly in ageing patients, disturbances in the labyrinthine system.

The extensive literature reveals no anxiolytic actions.

Clearly the combination of the two extracts, as proposed according to the invention, leads to a novel coergistic action, which is particularly suitable for the therapy of psychovegetative disturbances, which are based on anxiety states and stress situations, such as e.g. the psychovegetative exhaustion syndrome and probably is brought about by the influencing of peripheral and central control cycles.

A preferred embodiment of the combination is obtained through the use of extracts of Rhizoma zingiberis and Ginkgo bilobae, obtained by the combined extraction with ethanol/water or acetone/water mixtures or $CO_2$. These extracts are standardized to the essential known constituents.

Particular preference is given to the mixture of 100 mg of extract (oleoresin or $CO_2$ extract) of Rhizoma zingiberis and 40 mg of standard extract of Ginkgo bilobae administered in capsule form. The total daily dose recommended, according to the following analytical example, consists of 3 to 4 ingestion units (300 to 400 mg extract of Rhizoma zingiberis and 120 to 160 mg of extract of Ginkgo bilobae).

The novel indication of the combination product according to the invention is characterized in that vegetative disturbances in the area of the smooth musculature (gastrointestinal tract, contraction feeling in the throat, etc.) are removed in the same way as the accompanying headaches, irritability and sleep disturbances. It is particularly stressed that there is neither fatigue nor a feeling of relaxation in the musculature and in fact on the contrary there is an improvement to energy and vigilance.

Another advantage of the novelindication of the known combination product is its plant origin. This leads to an extremely low and virtually non-existent toxicity and a complete lack of carcinogenic or mutagenic effect.

PRODUCTION EXAMPLE

Figure 1:
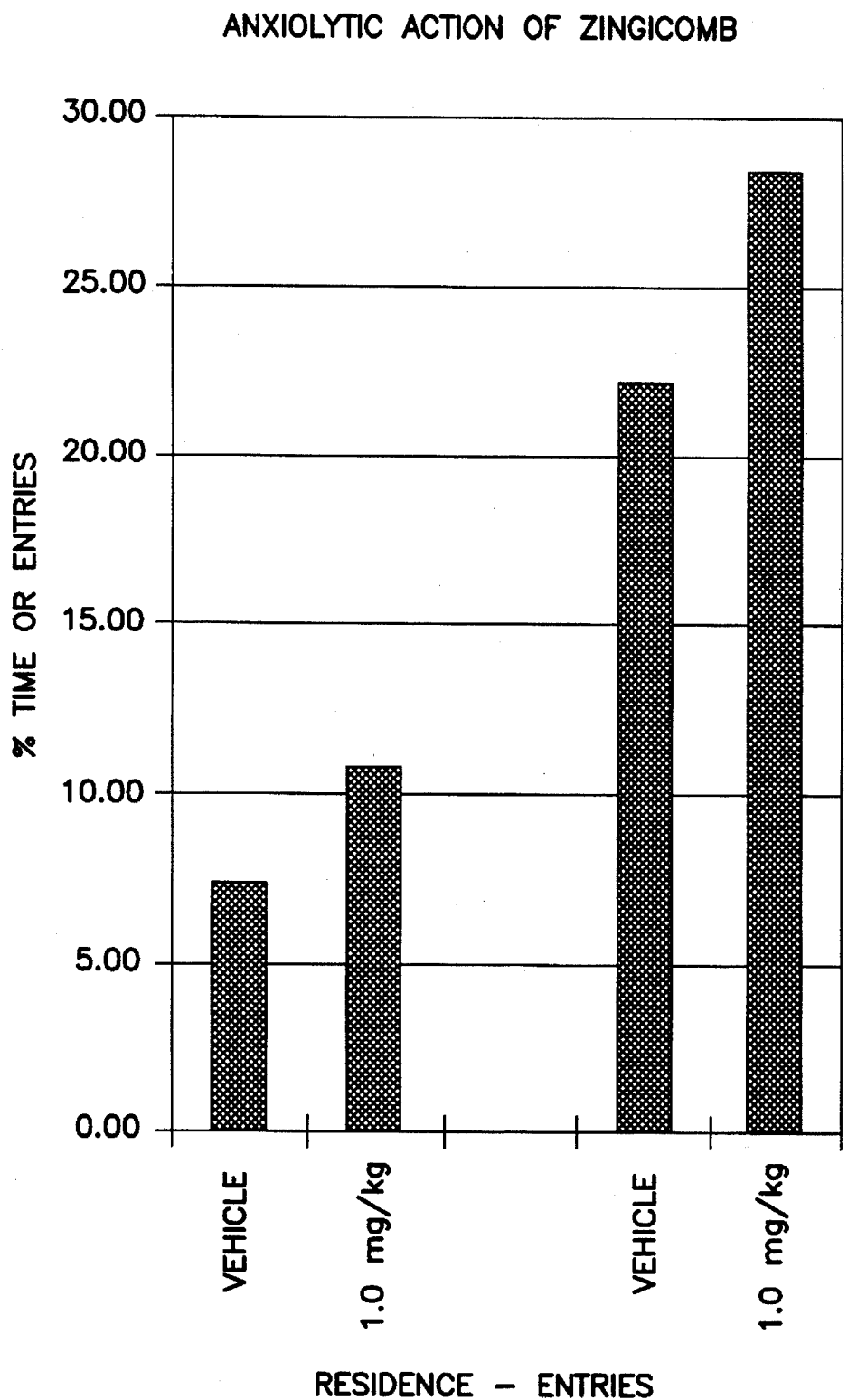
FIG. 1 Shows the anxiolytic action when the product according to the invention is administered according to the following production example compared with the administration of the vehicle alone.

Rhizoma zingiberis extract is obtained by ethanol/water extraction and subsequent concentration to an oleoresin or by $CO_2$ extraction. A similar Ginkgo.bilobae extract is obtained by standardized processes.

The pulverulent extracts are thoroughly mixed with one another in a weight ratio of Rhizoma zingiberis:Gingko bilobae of 10:4 and processed by known galenic processes to capsules containing in each case approximately 100 mg of Rhizoma zingiberis extract and approximately 40 mg of Ginkgo bilobae extract.

If required by the galenic formulation, the oleoresin or $CO_2$ extract is transformed into powder by microencapsulation or lyophilization.

USE EXAMPLE

The advantages of the invention are demonstrated by the following case example, as well as animal experiments:

CASE REPORT

A leading employee of a research and development department, age 51, 1.68 m, 69 kg visited his physician with the typical signs of a psychovegetative.exhaustion syndrome.

CASE HISTORY

At present the patient is responsible for three different, extensive projects. Two projects are linked with considerable work and organization, leading to a number of decisions with short to medium-term activities. These projects are strictly bound by deadlines and also not secured financially. Although there is no deadline pressure in connection with the third project, it still requires strategic planning, which is oriented way into the future.

The patient has complained for 14 days about uneasy sleep. He wakes up frequently, feels pressure in the stomach, thinks about the projects, whilst during the day he eats irregularly, concentrates greatly on the task involved and consumes large amounts of coffee. If he eats a large meal in the evening, he has little appetite, as well as stomach pains after taking food.

When problems arose in the personal sector at a decisive phase of the two projects, the situation worsened. The patient has the feeling of no longer being able to concentrate on important matters and he has doubts concerning his creativity. He has a feeling of nausea, associated with headaches and a feeling of giddiness in the morning when thinking over the daily tasks and possible conflict situations.

He hesitated to visit the doctor, because he was aware of the side effects of psychopharmaceuticals and he feared that they would worsen and not improve his present situation. As the patient had professional access to phytopharmaceutical extracts, the use thereof was suggested.

THERAPY

The physician prescribed a two day rest and thrice daily administration of the particularly preferred embodiment of the medicament used according to the invention, because the medicinal substances are known per se and have been described in numerous publications.

On the very next day the patient reported that he no longer had a full feeling, had undisturbed sleep and the morning nausea did not appear.

He was able to eat well, he reduced his coffee consumption and had the impression that he could more easily concentrate on the strategic project, whilst there were no longer any headaches.

On the next day this impression was reinforced and he indicated an increasing confidence and a feeling of being more efficient. Thinking over the situation led him to conclusions which he attributed to his positive action in connection with problems and his willingness to take decisions and risks. The physician therefore recommended that the medication be reduced to once daily and stop it completely after two further days.

ANIMAL EXPERIMENTS

The study was carried out with a behaviour model, which simulated for the animals a conflict situation between the urge to obtain information on the surrounding area and the inborn fear of the dangers of the unknown environment.

The model was developed by Handley and Mithani in 1984 (Effects of a2-adrenoceptor agonists and antagonists in a maze exploration model of "fear"-motivated behaviour, Naunyn-Schmiedeberg's Arch. Pharmacol. 327, 1–5 (1984)). It consists of a cross with two equally long arms (in the form of a + sign). Two of these arms are provided with walls, whereas two are open and without walls (terms in the English literature are "+maze" or "plus-maze"). The model arrangement is located freely at a certain height above the floor.

The evaluation of the behaviour is based on the observations of Handley and Mithani that rats avoid the open arms and prefer staying in the closed arms. The extent of the anxiety or fear can be expressed by the number of entries in the open arms compared with the total number of entries in the arms (open total ratio, OTR) and also by the percentage time spent by the animals in the open arms.

Both for the conventional anxiolytic such as benzodiazepines, barbiturates and ethanol and for anxiogenic substances such as yohimbine and pentylene tetrazole, the model reveals typical and validated effects, which are described in the literature (survey in Handley et al, loc.cit.).

In a study the product according to the invention (cf. production example) Zingicomb for short, was administered intragastrically and the results compared with the effects obtained with the administration of the vehicle only.

TEST ANIMALS

The test animals used were male Wistar rats weighing 250 to 300 g. The rats were kept in groups of 5 in separate cage trays and had free access to food and water. The area had a light/dark cycle of 12 hours in each case.

BEHAVIOURAL MODEL

The model corresponded to the "elevated plus-maze" type known from the literature and had two open arms with the dimensions 50×10 cm and two closed arms (dimensions 50×10×40 cm). The two arms of each type faced one another. The complete model was positioned freely 50 cm above the floor.

The behaviour of the animals was recorded with a video system and the tapes were evaluated by a computer system with respect to the number of entries in the arms and the residence times in the arms.

The complete arrangement was located in a 2×2 m area having a lighting of 15 W.

ADMINISTRATION OF THE PRODUCT

Zingicomb was so suspended in water on the test day by ultrasonic homogenization, that a dosage of 1.0 mg/kg was obtained when 2 ml/kg were supplied. Administration took place intragastrically by means of a gastric tube.

TEST SEQUENCE

On the test day the rats were transferred to individual cage trays, weighed and the vehicle or product administered by means of a gastric tube. After 60 min. the animals were brought individually into the examination area and placed in the centre of the behavioural model, view being directed onto one of the closed arms. During the following 5 minutes the number of entries and the residence times in the closed and open arms were recorded by means of the video system with the computer located outside the area.

RESULTS

The drawing shows the results with respect to the residence time in the open arms and the number of entries into the open arms as a percentage of all entries into the arms (mean value). What is given is the mean value of the percentage of the total time (5 min.) spent by the animals in the open arms. On the basis of the theory and validation of the model, an anxiolytic effect should lead to an increase in the percentage.

In accordance with this expectation, the results show an anxiolytic effect of Zingicomb. The dose of 1.0 mg/kg leads to a marked rise of about 46% in the residence time compared with the times obtained when only the vehicle was administered (FIG. 1).

The data concerning the number of entries into the arms also proved that the dose of 1.0 mg/kg of Zingicomb clearly increases the attractiveness of the open arms compared with the vehicle. The entries are approximately 28% more frequent than without Zingicomb administration.

The summary of the findings obtained gives, despite the small number of tested animals per dose (1.0 mg, n=6, vehicle n=12) gives a significant effect on the behaviour in the model when administering Zingicomb compared with the administration of the vehicle only.

As a result of the novel use of the described combination product according to the invention a rapid, problem-free therapy of fear and anxiety states, particularly psychovegetative exhaustion syndrome is to be expected, the disadvantages of the known tranquillizers, such as sedation, fatigue and tiredness, which would prejudice the result of the therapy in many cases, are not to be expected in the way in which this has taken place in investigations up to now. The features of the invention disclosed in the description, claims and drawing can be essential to the implementation of the different embodiments of the invention either singly or in the form of random combinations.

We claim:

1. A method for treating anxiety in a patient, said method comprising a step of:
   administering to the patient a medicament including active substances of Rhizoma zingiberis and Ginkgo bilobae;
   wherein the medicament is administered in an amount effective to result in anxiolytic activity.

2. The method according to claim 1, wherein the medicament includes a combination of extracts of Rhizoma zingiberis and Ginkgo bilobae.

3. The method according to claim 2, wherein the active substances or extracts are present in an ingestion unit in solid or liquid medicinal form suitable for peroral administration.

4. The method according to claim 3, wherein the ingestion unit is a capsule.

5. The method according to claim 2, wherein the Rhizoma zingiberis extract content is between 50 and 200 mg per ingestion unit.

6. The method according to claim 5, wherein the Rhizoma zingiberis extract content is about 100 mg per ingestion unit.

7. The method according to claim 2, wherein the Ginkgo bilobae extract content is between 10 and 100 mg per ingestion unit.

8. The method according to claim 7, wherein the Ginkgo bilobae extract content is about 40 mg per ingestion unit.

9. The method according to claim 2, wherein the extract is obtained from Rhizoma zingiberis by an ethanol/water or acetone/water extraction and is essentially present as an oleoresin.

10. The method according to claim 9, wherein the oleoresin extract from Rhizoma zingiberis is transformed into a suitable galenic form by microencapsulation, granulation or lyophilization.

11. The method according to claim 10, wherein the $CO_2$ extract from Rhizoma zingiberis is transformed into a suitable galenic form by microencapsulation, granulation or lyophilization.

12. The method according to claim 2, wherein the extract is obtained from Rhizoma zingiberis by extraction with $CO_2$.

13. A method for treating anxiety in a patient, said method comprising a step of:

administering to the patient a medicament including 50 to 200 mg Rhizoma zingiberis extract and 10 to 100 mg Ginkgo bilobae extract; wherein the Rhizoma zingiberis extract is obtained from an ethanol/water or acetone/water extraction and is essentially present as an oleoresin or the Rhizoma zingiberis extract is obtained by extraction with $CO_2$.

* * * * *